(12) United States Patent
Miura et al.

(10) Patent No.: US 8,673,960 B2
(45) Date of Patent: Mar. 18, 2014

(54) EXTERNAL LIQUID PREPARATION CONTAINING INDOMETHACIN

(75) Inventors: Hiroshi Miura, Fuji (JP); Makoto Kanebako, Fuji (JP)

(73) Assignee: Kowa Co., Ltd., Nagoya-shi (JP)

( * ) Notice: Subject to any disclaimer, the term of this patent is extended or adjusted under 35 U.S.C. 154(b) by 1075 days.

(21) Appl. No.: 12/067,722

(22) PCT Filed: Oct. 16, 2006

(86) PCT No.: PCT/JP2006/320539
§ 371 (c)(1),
(2), (4) Date: Mar. 21, 2008

(87) PCT Pub. No.: WO2007/046318
PCT Pub. Date: Apr. 26, 2007

(65) Prior Publication Data
US 2009/0137657 A1 May 28, 2009

(30) Foreign Application Priority Data
Oct. 17, 2005 (JP) .................................. 2005-301109

(51) Int. Cl.
*A61K 31/405* (2006.01)
(52) U.S. Cl.
USPC ........................................................ 514/420
(58) Field of Classification Search
USPC ........................................................ 514/420
See application file for complete search history.

(56) References Cited

U.S. PATENT DOCUMENTS

| | | | | |
|---|---|---|---|---|
| 4,917,886 A | * | 4/1990 | Asche et al. | 514/567 |
| 2005/0239868 A1 | * | 10/2005 | Shirai et al. | 514/420 |

FOREIGN PATENT DOCUMENTS

| | | |
|---|---|---|
| EP | 0 055 029 A2 | 6/1982 |
| EP | 1 541 144 A1 | 6/2005 |
| JP | 56-36411 | 4/1981 |
| JP | 58 124716 | 7/1983 |
| JP | 59 88419 | 5/1984 |
| JP | 61 200907 | 9/1986 |
| JP | 5-87483 | 12/1993 |
| JP | 6-9394 | 1/1994 |
| JP | 09-002946 | 1/1997 |
| JP | 2729859 | 12/1997 |
| WO | 94 23750 | 10/1994 |
| WO | WO 2004/101994 | * 2/2004 |

OTHER PUBLICATIONS

Arthur H. Kibbe (ed.): Monograph for polyethylene glycol in Handbook of Pharmaceutical Excipients, Third edition, pp. 392-419 (2000).*
Columibia Encyclopedia 6th Edition Online definition for "liquid" (http://www.encyclopedia.com/topic/liquid.aspx), accessed Aug. 22, 2009.*
Office Action issued on Mar. 6, 2012 for Japanese Patent Application No. 2007-540956 (with English translation).

* cited by examiner

*Primary Examiner* — Jeffrey S. Lundgren
*Assistant Examiner* — Sara E Townsley
(74) *Attorney, Agent, or Firm* — Oblon, Spivak, McClelland, Maier & Neustadt, L.L.P.

(57) ABSTRACT

The present invention provides an indomethacin-containing external liquid preparation which provides good feeling of use, which exhibits high percutaneous absorption of indomethacin, and which, particularly in a low-temperature environment, does not cause precipitation of crystals with time.
The present invention is drawn to an external liquid preparation containing indomethacin, a lower alcohol, water, a sulfite, and polyethylene glycol having an average molecular weight of 3,000 to 15,000.

5 Claims, No Drawings

EXTERNAL LIQUID PREPARATION CONTAINING INDOMETHACIN

TECHNICAL FIELD

The present invention relates to an external liquid preparation containing indomethacin. The preparation provides good feeling of use and promises good absorption. Moreover, the preparation will not produce crystal precipitation with time.

BACKGROUND ART

Indomethacin-containing external preparations have conventionally been commercialized in various forms, including gels, creams, and liquids. These product forms have their own characteristics. For example, gels and liquids dissolve indomethacin therein quite well because they contain large amounts of alcohol. Also, gels and liquids exhibit good percutaneous absorption property. However, when gels are applied to the skin, due to their inherent structure, gels tend to remain on the skin unevenly, resulting in unfavorable sensation and poor feeling of use. In contrast, creams contain large amounts of oily ingredients, which do not leave stickiness after use. Therefore, creams ensure good feeling of use. However, since creams can dissolve only insufficient amounts of indomethacin therein, they exhibit poor percutaneous absorption as compared with gels. Liquids have been widely employed because they provide excellent percutaneous absorption. However, they have disadvantages, including slow drying after application, causing running of the liquid preparation.

According to known typical practice, sulfites such as sodium bisulfite or similar additives are added to indomethacin-containing liquid preparations in order to prevent color change of the preparations or to decrease reduction in indomethacin content (Patent Document 1). However, when liquid preparations containing both indomethacin and a sulfite are stored at a low temperature, crystals are precipitated with time. To prevent this phenomenon, a variety of precipitation preventive measures have been employed.

In order to prevent crystal precipitation of indomethacin-containing external liquid preparations, several approaches have heretofore been proposed. Examples of products which are produced through such known techniques include an indomethacin-containing external liquid preparation in which a lower alcohol-water vehicle formed of indomethacin, a vitamin E compound, and a middle-chain fatty acid ester (which serves as a percutaneous absorption enhancer) is employed as a base composition of the preparation, and a surfactant such as polyoxyethylene hydrogenated castor oil is incorporated thereto (Patent Document 2); and an external liquid preparation in which indomethacin is combined with additives such as a lower alcohol (or acetone), crotamiton, and glycols (Patent Document 3). However, use of surfactants such as polyoxyethylene hydrogenated castor oil, or crotamiton is desirably avoided, because they might irritate the skin.

As mentioned above, there have not yet been provided satisfactory indomethacin-containing external liquid preparations which provide good feeling of use, which exhibit high percutaneous absorption of the active ingredient, and which under any conditions do not cause precipitation of crystals with time.

[Patent Document 1] JP-A-SHO59-88419
[Patent Document 2] JP-A-HEI6-9394
[Patent Document 3] JP-A-SHO58-124716

DISCLOSURE OF THE INVENTION

Problems to be Solved by the Invention

As described above, there have been demanded indomethacin-containing external liquid preparations which provide good feeling of use, which exhibit high percutaneous absorption of the active ingredient, and which do not produce precipitated crystals with time particularly in a low-temperature environment.

Accordingly, an object of the present invention is to provide an indomethacin-containing external liquid preparation, which provides good feeling of use, which enables the active ingredient to be absorbed excellently, and which does not cause crystal precipitation with time even in an environment of low temperatures.

Means for Solving the Problems

The present inventors have performed extensive studies in an attempt to attain the above object, and have quite unexpectedly found that when polyethylene glycol having an average molecular weight of 3,000 to 15,000 is added to a preparation containing indomethacin, a lower alcohol, water, and a sulfite, crystal precipitation is effectively prevented particularly in a low-temperature environment and that the thus-prepared liquid preparation is quickly dried, does not run, and thus provides excellent feeling of use. The present invention has been accomplished on the basis of these findings.

Accordingly, the present invention provides an external liquid preparation comprising indomethacin, a lower alcohol, water, a sulfite, and polyethylene glycol having an average molecular weight of 3,000 to 15,000.

Effects of the Invention

The present invention provides an indomethacin-containing external liquid preparation which promises good feeling of use, which exhibits high percutaneous absorption of the active ingredient, and which does not produce, particularly in a low-temperature environment, precipitated crystals with time.

BEST MODE FOR CARRYING OUT THE INVENTION

Indomethacin content is generally 0.1 to 3 mass %, preferably 0.2 to 2 mass %, particularly preferably 0.5 to 1.5 mass %, on the basis of the total amount of the external liquid preparation of the present invention.

Examples of the C1 to C6 linear or branched alcohol include methanol, ethanol, isopropanol, and n-propanol. Of these, ethanol and isopropanol are particularly preferred. Lower alcohol content is generally 35 to 65 mass %, preferably 40 to 60 mass %, particularly preferably 45 to 55 mass %, on the basis of the total amount of the external liquid preparation of the present invention, in consideration of solubility and percutaneous absorbability of indomethacin.

Water content is generally 25 to 55 mass %, preferably 30 to 50 mass %, particularly preferably 35 to 45 mass % on the basis of the total amount of the external liquid preparation of the present invention in consideration of feeling of use and stability of the drug.

The total amount of a lower alcohol and water is 40 to 99.88 mass %, preferably 70 to 99 mass %, particularly preferably 80 to 95 mass % on the basis of the total amount of the external liquid preparation of the present invention in consideration of solubility and percutaneous absorbability of indomethacin, and feeling of use and stability of the drug.

Examples of the sulfite according to the present invention include sodium bisulfite, sodium sulfite, dried sodium sulfite, sodium pyrosulfite, and potassium pyrosulfite, with sodium bisulfite being particularly preferred. The sulfite content is generally 0.01 to 1 mass %, preferably 0.05 to 0.5 mass %, particularly preferably 0.1 to 0.3 mass % on the basis of the total amount of the external liquid preparation in order to stabilize indomethacin and to suppress change in the drug color.

According to the present invention, the average molecular weight of polyethylene glycol is 3,000 to 15,000, preferably 4,000 to 10,000. In order to prevent precipitation of crystals from the external liquid preparation with time, the average molecular weight is particularly preferably 6,000. As is disclosed in the Examples below, by restricting the average molecular weight of polyethylene glycol to fall within the above range, the external liquid preparation does not suffer crystal precipitation with time. Polyethylene glycol having an average molecular weight of 3,000 to 15,000 is solid at room temperature, and therefore, it cannot serve as a solvent for indomethacin. Moreover, it is not a surfactant. Nevertheless, when polyethylene glycol having a molecular weight falling within the above-specified range is incorporated, crystal precipitation of indomethacin is prevented. Such specific polyethylene glycols can be selected from among widely-employed moisturizers, thickeners, solubilizers, etc. Specific examples of commercially available polyethylene glycols include macrogol 4000, macrogol 6000 (these are products of NOF CORPORATION.), polyethylene glycol 8000 (product of ICN), polyethylene glycol 15000 (product of Merck). These polyethylene glycols may be employed singly or in combination of two or more species. The average molecular weight can be calculated through gel permeation chromatography or similar techniques.

No particular limitation is imposed on the polyethylene glycol content, and it is generally 0.01 to 2.5 mass %, preferably 0.05 to 2 mass %, more preferably 0.1 to 1.5 mass %, particularly preferably 0.5 to 1.5 masse on the basis of the total amount of the external liquid preparation of the present invention in order to prevent precipitation of crystals—which might otherwise occur with time—from the external liquid preparation of the present invention.

Proportions, by mass, of indomethacin content, sulfite content, and polyethylene glycol content on the basis of the total amount of the external liquid preparation are as follows. That is, when indomethacin content is taken as 1, sulfite is generally 0.003 to 10, preferably 0.025 to 2.5, particularly preferably 0.07 to 0.6; and polyethylene glycol content is generally 0.003 to 25, preferably 0.025 to 10, more preferably 0.07 to 3, particularly preferably 0.3 to 3, in order to ensure stabilization of indomethacin and to prevent crystal precipitation.

The external liquid preparation of the present invention may further contain a gelling agent, an oily ingredient, a neutralizing agent, a preservative, and a moistening agent, but are not limited thereto.

Examples of the gelling agent include acrylic acid polymers such as carboxyvinyl polymer, cellulose polymers such as hydroxypropylmethyl cellulose and ethyl cellulose, and polyvinyl alcohols.

Examples of the oily ingredient include hydrocarbons such as squalane and liquid paraffin; and esters such as isopropyl myristate, diisopropyl adipate, and octyldodecyl myristate.

Examples of the neutralizing agent include organic acids such as citric acid, phosphoric acid, tartaric acid, and lactic acid; inorganic acids such as hydrochloric acid; alkali hydroxides such as sodium hydroxide; and amines such as triethanolamine, diethanolamine, and diisopropanolamine.

Examples of the preservative include p-hydroxybenzoate esters and benzalkonium chloride.

Examples of the moistening agent include polyhydric alcohols such as glycerin, ethylene glycol, propylene glycol, oleyl alcohol, 1,3-butylene glycol, and isopropylene glycol.

The pH of the external liquid preparation of the present invention is generally pH 4 to 8, preferably pH 5 to 7, in consideration of stability of indomethacin, skin irritation, and other factors.

No particular limitation is imposed on the dose and frequency of the external liquid preparation of the present invention, and these may be determined appropriately depending on various conditions such as pathological conditions and sites to be administered.

EXAMPLES

The present invention will next be described in more detail by way of examples, which should not be construed as limiting the invention thereto.

Example 1

Indomethacin (1 g) and l-menthol (3 g) were dissolved in a mixture of diisopropyl adipate (5 g) and isopropanol (50 g). Separately, hydroxypropylmethyl cellulose (0.1 g) and polyethylene glycol 4000 (macrogol 4000, product of NOF CORPORATION.) (1 g) were dissolved in purified water (33 g), and the solution was mixed with the indomethacin-containing solution, to thereby form a uniform mixture. Subsequently, sodium bisulfite (sodium bisulfite, product of KATAYAMA CHEMICAL INDUSTRIES) (0.2 g) was added to the mixture. The pH of the mixture was adjusted to 5.8 with sodium hydroxide, and purified water was added to the mixture so as to adjust the amount to 100 g. The mixture was sufficiently mixed with stirring, to thereby yield a liquid preparation.

Example 2

The procedure of Example 1 was repeated, except that polyethylene glycol 6000 (macrogol 6000, product of NOF CORPORATION.) was employed instead of polyethylene glycol 4000, to thereby yield a liquid preparation.

Example 3

The procedure of Example 1 was repeated, except that polyethylene glycol 8000 (polyethylene glycol 8000, product of ICN) was employed instead of polyethylene glycol 4000, to thereby yield a liquid preparation.

Example 4

The procedure of Example 1 was repeated, except that polyethylene glycol 10000 (polyethylene glycol 10000, product of Merck) was employed instead of polyethylene glycol 4000, to thereby yield a liquid preparation.

Comparative Example 1

The procedure of Example 1 was repeated, except that polyethylene glycol 4000 was not employed, to thereby yield a liquid preparation.

Comparative Example 2

The procedure of Example 1 was repeated, except that polyethylene glycol 2000 (polyethylene glycol 2000, product of Wako Pure Chemical Industries, Ltd.) was employed instead of polyethylene glycol 4000, to thereby yield a liquid preparation.

Comparative Example 3

The procedure of Example 1 was repeated, except that polyethylene glycol 20000 (macrogol 20000, product of Sanyo Chemical Industries, Ltd.) was employed instead of polyethylene glycol 4000, to thereby yield a liquid preparation.

Experimental Example 1

In order to check outer stability of the above-prepared liquid preparations on the basis of their appearance, each liquid preparation of Examples 1 to 4 and Comparative Examples 1 to 3 was charged into a glass bottle (a 2K bottle), and occurrence of crystal precipitation was observed. Crystal precipitation was evaluated by visual inspection. Liquid preparations in which no crystal precipitation had been observed are marked with "10," and liquid preparations in which crystal precipitation had been observed are marked with "X." Visual inspection was performed immediately after preparation, after one-week storage at −20° C., after two-week storage at −20° C., and after three-week storage at −20° C. The results are shown in Table 1.

As is clear from Table 1, in liquid preparations containing polyethylene glycols having an average molecular weight of 4,000 (Example 1), 6,000 (Example 2), 8,000 (Example 3), and 10,000 (Example 4), respectively, crystal precipitation was not observed and they were found to be stable with time. On the other hand, in the liquid preparation containing no polyethylene glycol (Comparative Example 1), and liquid preparations containing polyethylene glycols having an average molecular weight of 2,000 (Comparative Example 2) and 20,000 (Comparative Example 3), respectively, crystal precipitation was observed. Notably, the liquid preparation of Example 2 was found very stable, as crystal precipitation was not observed even after storage at −20° C. for two months.

Moreover, external liquid preparations of Examples 1 to 4 were quickly dried after application and conveniently managed as they did not run on the skin. Moreover, they were found to provide excellent percutaneous absorption of indomethacin.

The invention claimed is:

1. An external liquid preparation comprising:
   indomethacin,
   a lower alcohol,
   water,
   a sulfite that is sodium bisulfite or sodium pyrosulfite (sodium metabisulfite), and
   polyethylene glycol having an average molecular weight of 3,000 to 15,000.

2. The external liquid preparation as described in claim 1, wherein the sulfite is sodium bisulfite.

3. The external liquid preparation as described in claim 1, wherein the polyethylene glycol is contained in an amount of 0.01 to 2.5 mass %.

4. The external liquid preparation as described in claim 1, that comprises:
   0.1 to 3 mass % indomethacin,
   35 to 65 mass % lower alcohol, and
   25 to 55 mass % water.

5. The external liquid preparation as described in claim 1, wherein the indomethacin, sulfite and polyethylene glycol are present in the following proportions by mass:
   indomethacin: sulfite at 0.003 to 10;
   indomethacin: polyethylene glycol at 0.003 to 25.

* * * * *

TABLE 1

| | | Ex. 1 | Ex. 2 | Ex. 3 | Ex. 4 | Comp. Ex. 1 | Comp. Ex. 2 | Comp. Ex. 3 |
|---|---|---|---|---|---|---|---|---|
| Indomethacin | | 1 | 1 | 1 | 1 | 1 | 1 | 1 |
| Isopropanol | | 50 | 50 | 50 | 50 | 50 | 50 | 50 |
| Sodium bisulfite | | 0.2 | 0.2 | 0.2 | 0.2 | 0.2 | 0.2 | 0.2 |
| Polyethylene glycol 4000 | | 1 | — | — | — | — | — | — |
| Polyethylene glycol 6000 | | — | 1 | — | — | — | — | — |
| Polyethylene glycol 8000 | | — | — | 1 | — | — | — | — |
| Polyethylene glycol 10000 | | — | — | — | 1 | — | — | — |
| Polyethylene glycol 2000 | | — | — | — | — | — | 1 | — |
| Polyethylene glycol 20000 | | — | — | — | — | — | — | 1 |
| Hydroxypropylmethyl cellulose | | 0.1 | 0.1 | 0.1 | 0.1 | 0.1 | 0.1 | 0.1 |
| l-Menthol | | 3 | 3 | 3 | 3 | 3 | 3 | 3 |
| Diisopropyl adipate | | 5 | 5 | 5 | 5 | 5 | 5 | 5 |
| Sodium hydroxide | | Suitable Amount | Suitable Amount | Suitable Amount | Suitable Amount | Suitable Amount | Suitable Amount | Suitable Amount |
| Purified water | | Total 100 g | Total 100 g | Total 100 g | Total 100 g | Total 100 g | Total 100 g | Total 100 g |
| Outer stability as determined by appearance | Immediately after preparation | ○ | ○ | ○ | ○ | ○ | ○ | ○ |
| | −20° C. 1 week after | ○ | ○ | ○ | ○ | X | ○ | X |
| | 2 week after | ○ | ○ | ○ | ○ | X | ○ | X |
| | 3 week after | ○ | ○ | ○ | ○ | X | X | X |